US007238523B1

(12) United States Patent
Kulesz-Martin

(10) Patent No.: US 7,238,523 B1
(45) Date of Patent: Jul. 3, 2007

(54) P53AS PROTEIN AND ANTIBODY THEREFOR

(75) Inventor: Molly F. Kulesz-Martin, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 989 days.

(21) Appl. No.: 08/644,289

(22) Filed: May 10, 1996

Related U.S. Application Data

(63) Continuation-in-part of application No. 08/195,952, filed on Feb. 11, 1994, now abandoned, which is a continuation-in-part of application No. 08/100,496, filed on Aug. 2, 1993, now abandoned.

(51) Int. Cl.
*C12N 15/85* (2006.01)

(52) U.S. Cl. .................... 435/325; 435/252.5; 435/7.1; 536/23.1; 536/23.5

(58) Field of Classification Search ............... 536/23.1, 536/23.5; 530/324; 435/7.23, 252.3, 7.1, 435/325
See application file for complete search history.

(56) References Cited

FOREIGN PATENT DOCUMENTS

| EP | A-O-529 160 | 3/1993 |
|----|-------------|--------|
| EP | 0 652 232 A1 | 5/1995 |
| WO | 92/13970 | 8/1992 |

OTHER PUBLICATIONS

Harris, C.C. "Structure and function of the p53 tumor suppressor gene: clues for rational cancer therapeutic strategies" Journal of the National Cancer Institute. vol. 88. No. 20. pp. 1442-1455, Oct. 16, 1996.*
Sambrook et al. "Molecular Cloning: A laboratory Manual" Second Edition. Cold Spring Harbor Press, 1989.*
Sambrook et al, eds, 1987, Molecular Cloning, A laboratory manual, 2nd ed, Cold Spring Harbor Laboratory Press, Cold spring Harbor, pp. 1.3, 1.21.*
Harris et al. J. of The Am Society of Nephrology 6:1125-33, 1995.*
Ahn et al. Nature Genetics 3(4):283-91, 1993.*
Cawthon et al. Genomics 9(3):446-60, 1991.*
Hupp et al, 1992, Cell, 71: 875-886.*
Funk, WD et al, 1992, Mol Cell Biol, 12: 2866-2871.*
Sambrook et al, eds, Molecular cloning, A laboratory manual, 2$^{nd}$ ed., Cold Spring Harbor Laboratory Press, 1989, p. 16.3-16.4, 17.10-17.28, 17.36.*
Kulesz-Martin, et al., "Endogenous p53 Protein Generated from Wild-Type Alternatively Spliced p53 RNA in Mouse Epidermal Cells", Mol. Cell. Bio., pp. 1698-1708, 1994.
Wu, et al., "Activities and Response to DNA Damage of Latent and Active Sequence-Specific DNA Binding Forms of Mouse p53", Proc. Natl. Acad. Sci, vol. 94, pp. 8982-8987, 1997.
Arai, N., et al., (1986) Immunologically Distinct p53 Molecules Generated by Alternative Splicing. Mol. and Cell. Biol. 6, 3232-3239.
Balmain, A., et al. (1982) Cloning and Characterization of the Abundant Cytoplasmic 7S RNA from Mouse Cells. Nucleic Acids Res. 10, 4259-4277.
Bargonetti, J., et al. (1992) Site-Specific Binding of Wild-Type p53 to Cellular DNA is Inhibited by SV40 T Antigen and Mutant p53. Genes & Dev. 6, 1886-1898.
Bayle, J. et al., (1995) The Carboxyl-Terminal Domain of the p53 Protein Regulates Sequence-Specific DNA Binding Through its Nonspecific Nucleic Acid Binding Activity, Proc. Nat. Acad. Sciences of USA, vol. 92, No. 12, p. 5729-5733.
Burns, P.A., et al. (1991) Loss of Heterozygosity and Mutational Alterations of the p53 Gene in Skin Tumours of Interspecific Hybrid Mice. Oncogene 6, 2363-2369.
Crook, T., et al. (1991) Modulation of Immortalizing Properties of Human Papillomavirus Type 16E7 by p53 Expression. J. Virol. 6, 505-510.
Davies, R., et al. (1993) Antioxidants can Delay Liver Cell Muturation Which in Turn Affects γ-glutamyltranspeptidase Expression. Carcinogen. 14,47-52.
Eliyahu, D., et al. (1988) Meth A Fibrosarcoma Cells Express Two Transforming Mutant p53 Species. Oncogene 3, 313-321.
Farmer, G., et al. (1992) Wild-Type p53 Activates Transcription in vitro. Nature 358, 83-86.
Finlay, C.A., et al. (1989) The p53 Proto-Oncogene can Act as a Suppressor of Transformation. Cell 57, 1083-1093.
Fontoura, B.M.A. et al. (1992) p53 is Covalently Linked to 5.8S rRNA. Mol. Cell. Biol. 12, 5145-5151.
Foord, O.S., et al. (1991) A DNA Binding Domain is Contained in the C-Terminus of Wild Type p53 Protein. Nucleic Acids Res. 19, 5191-5198.
Foulkes, N.S., et al. (1992) More is Better: Activators and Repressors from the Same Gene. Cell 68, 411-414.

(Continued)

*Primary Examiner*—Jeffrey Siew
*Assistant Examiner*—Minh-Tam Davis
(74) *Attorney, Agent, or Firm*—Michael L. Dunn

(57) ABSTRACT

The invention comprises plasmids and viral vectors containing an animal p53as cDNA sequence. A portion of the p53as sequence may be identified to a position of wild type p53 gene from the same animal. In preferred embodiments, the p53as is mouse or human p53as. A preferred viral vector is baculovirus vector. The invention further includes antibodies both polyclonal and monoclonal, to p53as and to at least a portion of human p53 intron 10 sequence encoding SLR-PFKALVREKGHRPSSHSC (SEQ. I.D. NO. 1) which is related to p53as sequences and plasmids and viral vectors containing such sequences. All of the above find utility in studying p53 and p53as and their relative expressions which is believed important for detection and control of malignant cells and their susceptibility to treatment agents. The antibodies can detect the presence of p53as and related sequences and when injected into cells could cause cell cycle arrest and the plasmids and viral vectors, with appropriate promoters, can cause expression of the p53as and p53 intron 10 sequences which can affect cell growth and perhaps arrest certain malignancies.

14 Claims, 9 Drawing Sheets

OTHER PUBLICATIONS

Gannon, J.V. et al. (1990) "Activating Mutations in p53 Produce a Common Conformational Effect. A Monoclonal Antibody Specific for the Mutant Form," EMBO 9:1595-1602.

Hainaut, P., et al. (1992) Interaction of Heat-Shock Protein 70 with p53 Translated in vitro evidence for Interaction with Dimeric p53 and for a Role in the Regulation of p53 Conformation. EMBO J. 11, 3513-3520.

Han, K., et al. (1990) Altered Levels of Endogenous Retrovirus-like Sequence (VL30) RNA During Mouse Epidermal Cell Carcinogenesis. Mol. Carcinogenesis 3:75-82.

Han, K., et al. (1992) Altered Expression of Wild-type p53 Tumor Supressor Gene During Murine Epithelial Cell Transformation. Cancer Research 52, 749-753.

Han, K., et al. (1992) Alternatively Spliced p53 RNA in Transformed and Normal Cells of Different Tissue Types. Nucleic Acids Res., 20(8), 1979-1981.

Hupp, T.R., et al. (1992) Regulation of the Specific DNA Binding Function of p53. Cell 71, 875-886.

Jenkins, J.R., et al. (1984) Cellular Immortalization by a cDNA Clone Encoding the Transformation-Associated Phosphoprotein p53. Nucleic Acids Res. 12, 5609-5626.

Kastan, M.B., et al. (1991) Participation of p53 Protein in the Cellular Response to DNA Damage. Cancer Research 51, 6304-6311.

Kastan, M.B. et al. (1992) A Mammalian Cell Cycle Checkpoint Pathway Utilizing p53 and GADD45 is Defective in *Ataxia-telangiectasia*. Cell 71, 587-597.

Kulesz-Martin, M. et al. (1985) Mouse Cell Clones for Improved Quantitation of Carcinogen-Induced Altered Differentiation. Carcinogenesis 6, 1245-1254.

Kulesz-Martin, M. et al. (1986) Retinoic Acid Enhancement of an Early Step in the Transformation of Mouse Epidermal Cells *in vitro*. Carcinogenesis 7, 1425-1429.

Kulesz-Martin, M. et al. (1989) Pemphigoid, Pemphigus and Desmoplakin as Antigenic Markers of Differentiation in Normal and Tumorigenic Mouse Keratinocyte Lines. Cell Tissue Kinet. 22, 279-290.

Kulesz-Martin, M. et al. (1991) Tumor Progression of Murine Epidermal Cells After Treatment *in vitro* with 12-O-Tetradecanoylphorbol-13-Acetate or Retinoic Acid. Cancer Research 51, 4701-4706.

Kulesz-Martin, M. et al. (1983) Properties of Carcinogen Altered Mouse Epidermal Cells Resistant to Calcium-Induced Terminal Differentiation. Carcinogen 4, 1367-1377.

Kulesz-Martin, M. et al., (1994) Endogenous Mouse p53 Protein Generated by Alternative Splicing, J. Cellular Biochemistry Supplement, vol. 0, No. 18c, p. 170.

Lane, D.P. (1992) p53, Guardian of the Genome. Nature 358, 15-16.

Milne, D.M., et al. (1992) Mutation of the Casein Kinase II Phosphorylation Site Abolishes the Anti-Proliferative Activity of p53. Nucleic Res. 20, 5565-5570.

Milner, J. (1991) The Role of p53 in the Normal Control of Cell Proliferation. Current Opinion in Cell Biology 3, 282-286.

Milner, J. (1984) Different Forms of p53 Detected by Monoclonal Antibodies in Non-Dividing and Dividing Lymphocytes. Nature 20, 143-145.

Milner, J. et al. (1991) Cotranslation of Activated Mutant p53 with Wild Type Drives the Wild-Type p53 Protein into the Mutant Conformation. Cell 65, 765-774.

Momand, J., et al. (1992) The mdm-2 Oncogene Product forms a Complex with the p53 Protein and Inhibits p53-Mediated Transactivation. Cell 69, 1237-1245.

Nigro, J.M., et al. (1992) Human p53 and CDC2Hs Genes Combine to Inhibit the Proliferation of *Saccharomyces cerevisiae*. Mol. and Cell Biol. 12, 1357-1365.

Oren, M. et al. (1983) Molecular Cloning of a cDNA Specific for the Murine p53 Cellular Tumor Antigen. Proc. Natl. Acad. Sci. USA, 80, 56-59.

Prives, C., et al. (1993) The p53 Tumor Suppressor Protein: Meeting Review. Genes & Dev. 7:529-534.

Ro, Y.S., et al. (1993) p53 Protein Expression in Benign and Malignant Skin Tumours. Br. J. Dermatol. 12, 237-241.

Ruggeri, B., et al. (1991) Alterations of the p53 Tumor Suppressor Gene During Mouse Skin Tumor Progression. Cancer Research 51, 6615-6621.

Schneider, B.L., et al. (1993) 7,12-Dimethylbenz[α]anthracene-Induced Mouse Keratinocyte Transformation Without Harvey ras Protoonocgene Mutations. J. Invest. Dermatology, 101:595-599, 1993.

Seto, E., et al. (1992) Wild-Type p53 Binds to the TATA-Binding Protein and Represses Transcription. Proc. Natl. Acad. Sci. 89, 12028-12032.

Soussi, T., et al. (1990) Structural Aspects of the p53 Protein in Relation to Gene Evolution. Oncogene 5, 945-952.

Stenger, J.E., et al. (1992) Formation of Stable p53 Homotetramers and Multiples of Tetramers. Mol. Carcinogen. 5, 102-106.

Stephen, C.W., et al. (1992) Mutant Conformation of p53. Precise Epitope Mapping Using a Filamentous Phage Epitope Library. J. Mol. Biol. 225,577-583.

Sturzbecher, H.S., et al. (1992) A C-Terminal α-Helix Plus Basic Region Motif is the Major Structural Determinant of p53 Tetramerization. Oncogene 7, 1513-1523.

Vogelstein, B. (1990) A Deadly Inheritance. Nature 348, 681-682.

Vogelstein, B., et al. (1992) p53 Function and Dysfunction. Cell 70, 523-526.

Wade-Evans, A., et al. (1985) Precise Epitope Mapping of the Murine Transformation-Associated Protein, p53. EMBO J. 4,699-706.

Weintraub, H., et al. (1991) The MCK Enhancer Contains a p53 Responsive Element. Proc. Natl. Acad. Sci. 88, 4570-4571.

Wolf, D., et al. (1985) Isolation of a Full-Length Mouse cDNA Clone Coding for an Immunologically Distinct p53 Molecule. Mol. and Cell Biol. 51, 127-132.

Wolf, D., et al. (1984) Reconstitution of p53 Expression in a Nonproducer Ab-MuLV-Transformed Cell Line by Transfection of a Functional p53 Gene. Cell 38, 119-126.

Wu, Y. et al., (1994) Physiological Protein Variant of the Mouse p53 Tumor Suppressor Gene, Proc. of the American Assoc. for Cancer Research, Annual Mtg., vol. 35, p. 605.

Wu, Y. et al. (1994) Wild-Type Alternatively Spliced p53: Binding to DNA and Interaction with the Major p53 Protein in vitro and in Cells, The EMBO Journal, vol. 13, No. 20, p. 4823-4830.

Yonish-Rouach, E., et al. (1993) p53-Mediated Cell Death: Relationship to Cell Cycle Control. Mol. and Cell. Biol. 13, 1415-1423.

Yonish-Rouach, E., et al. (1991) Wild-Type p53 Induces Apoptosis of Myeloid Leukaemic Cells that is Inhibited by Interleukin-6. Nature 352, 345-347.

Zambetti, G.P., et al. (1992) Wild-Type p53 Mediates Positive Regulation of Gene Expression Through a Specific DNA Sequence Element. Genes & Dev. 6, 1143-1159.

* cited by examiner

Figure 3. p53as Protein Complex with DNA is Shifted by anti-p53as (ApAs) and Abrogated by anti-p53 Antibodies PAb246 (246) and CM5 but not Mutant Conformation-Specific PAb240 (240).

Lack of Interaction of p53as and p53 Proteins Mixed Posttranslationally.

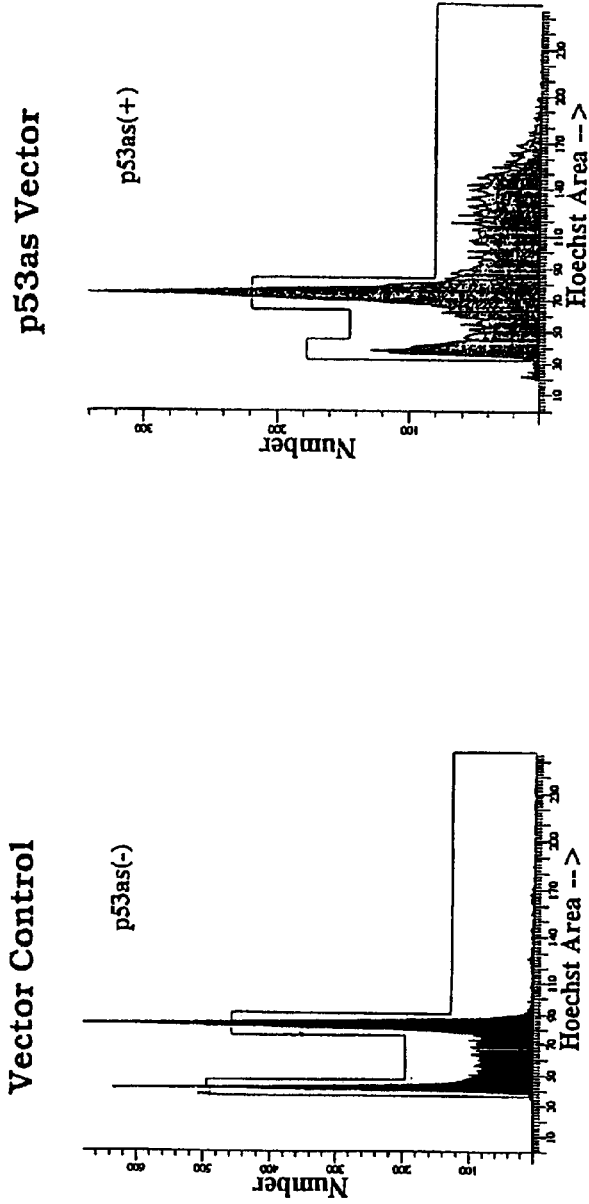
Figure 8. Cell Cycle Analysis of Insect Cells after Infection with a Baculovirus Vector Containing p53as cDNA

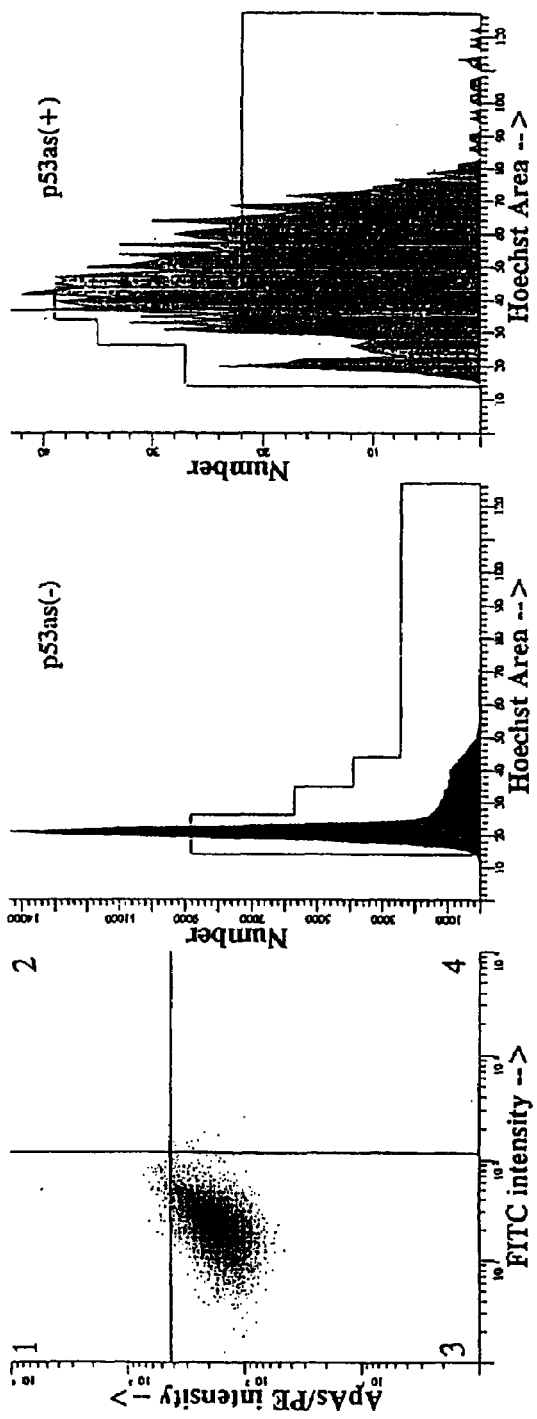
Figure 9. Cell Cycle Analysis of Mouse Squamous Carcinoma Cells after Transfection with a Plasmid Construct Containing p53as cDNA

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 20
      (B) TYPE: amino acids
      (C) STRANDEDNESS: unknown
      (D) TOPOLOGY: unknown (ii) MOLECULE TYPE: peptide (iii) HYPOTHETICAL: no (iv) ANTI-SENSE: no (v) FRAGMENT TYPE: peptide (vi) ORIGINAL SOURCE:
      (A) ORGANISM: human
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(vii) IMMEDIATE SOURCE:
      (A) LIBRARY: deduced translation from nucleotides
          in Genbank nucleic acid database accession
          #54156, Locus HSP53G
      (B) CLONE:

(viii) POSITION IN GENOME:
      (A) CHROMOSOME/SEGMENT: human p53 gene, intron 10
      (B) MAP POSITION: 18,503 to 18,562
      (C) UNITS: nucleotides (ix) FEATURE:
      (A) NAME/KEY:
      (B) LOCATION:
      (C) IDENTIFICATION METHOD:
      (D) OTHER INFORMATION:

(x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO:

(xi) SEQUENCE DESCRIPTION: SEQ ID NO: 1:

Ser Leu Arg Pro Phe Lys Ala Leu Val Arg Glu Lys Gly His Arg Pro
1           5                  10               15

Ser His Ser Cys
        20

(2) INFORMATION FOR SEQ ID NO: 2:

(i) SEQUENCE CHARACTERISTICS:
      (A) LENGTH: 38
      (B) TYPE: nucleotides

```
            (C) STRANDEDNESS:  unknown
            (D) TOPOLOGY:  unknown (ii) MOLECULE TYPE:  nucleic acids (iii) HYPOTHETICAL:

(iv) ANTI-SENSE:

(v) FRAGMENT TYPE:

(vi) ORIGINAL SOURCE:
            (A) ORGANISM:  murine
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:   synthesized (vii) IMMEDIATE SOURCE: Genbank Accession #K01700
            (A) LIBRARY:
            (B) CLONE:

(viii) POSITION IN GENOME:
            (A) CHROMOSOME/SEGMENT:
            (B) MAP POSITION:  nucleotides 1028-1061 in murine
                p53 gene
            (C) UNITS: nucleotides (ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 2:

AGTCAGGCCT TAGAGTTAAA GGATGCCCAT GCTACAGA                                38

(2) INFORMATION FOR SEQ ID NO: 3:

(i) SEQUENCE CHARACTERISTICS:
            (A) LENGTH:  28
            (B) TYPE:  nucleotide
            (C) STRANDEDNESS:  unknown
            (D) TOPOLOGY:  unknown (ii) MOLECULE TYPE:  nucleic acids (iii) HYPOTHETICAL:

(iv) ANTI-SENSE:

(v) FRAGMENT TYPE:

(vi) ORIGINAL SOURCE:
            (A) ORGANISM:  murine
            (B) STRAIN:
            (C) INDIVIDUAL ISOLATE:
            (D) DEVELOPMENTAL STAGE:
            (E) HAPLOTYPE:
            (F) TISSUE TYPE:
```

```
            (G) CELL TYPE:
            (H) CELL LINE:
            (I) ORGANELLE:

(vii) IMMEDIATE SOURCE:  synthesized
            (A) LIBRARY:  Genbank Accession #K01700
            (B) CLONE:

(viii) POSITION IN GENOME:
            (A) CHROMOSOME/SEGMENT:
            (B) MAP POSITION:  -111 to -91 upstream of murine
                p53 coding region
            (C) UNITS:  nucleotides (ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 3:

AGTCGAATTC ATTGGGACCA TCCTGGCT                                           28

(2) INFORMATION FOR SEQ ID NO: 4:

(i) SEQUENCE CHARACTERISTICS:
            (A) LENGTH:  30
            (B) TYPE:  nucleotide
            (C) STRANDEDNESS:  unknown
            (D) TOPOLOGY:  unknown (ii) MOLECULE TYPE:  nucleic acids (iii) HYPOTHETICAL:

(iv) ANTI-SENSE:  yes (v) FRAGMENT TYPE:

(vi) ORIGINAL SOURCE:
            (A) ORGANISM:  murine
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:  synthesized
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:  1071-1100 in murine p53 gene
            (C) IDENTIFICATION METHOD:
            (D) OTHER INFORMATION:
```

```
    (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 4:

AGTCGGATCC TGGAGTGAGC CCTGCTGTCT                                        30

(2) INFORMATION FOR SEQ ID NO: 5:

(i) SEQUENCE CHARACTERISTICS:
        (A) LENGTH:  10
        (B) TYPE:  nucleotides
        (C) STRANDEDNESS:  unknown
        (D) TOPOLOGY:  unknown (ii) MOLECULE TYPE:  nucleic acids (iii) HYPOTHETICAL:

(iv) ANTI-SENSE:

(v) FRAGMENT TYPE:

(vi) ORIGINAL SOURCE:
        (A) ORGANISM:  human
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:  El-Deiry, WS, et al.
        (B) TITLE:
        (C) JOURNAL:  Nature
        (D) VOLUME:  358
        (E) ISSUE:
        (F) PAGES:  83-86
        (G) DATE:  1992
        (H) DOCUMENT NUMBER:
        (I) FILING DATE:
        (J) PUBLICATION DATE:  1992
        (K) RELEVANT RESIDUES IN SEQ ID NO:

(xi) SEQUENCE DESCRIPTION: SEQ ID NO: 5:

AGGCATGCCT                                                              10
```

(2) INFORMATION FOR SEQ ID NO: 6: -P53 DNA binding sequence:

(i) SEQUENCE CHARACTERISTICS:
        (A) LENGTH: 50
        (B) TYPE: nucleotides
        (C) STRANDEDNESS: unknown
        (D) TOPOLOGY: unknown (ii) MOLECULE TYPE: nucleic acids (iii) HYPOTHETICAL:

(iv) ANTI-SENSE:

(v) FRAGMENT TYPE:

(vi) ORIGINAL SOURCE:
        (A) ORGANISM: human
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE: synthesized
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS: Zambetti, G., et al.
        (B) TITLE:
        (C) JOURNAL: Genes & Dev.
        (D) VOLUME: 6
        (E) ISSUE:
        (F) PAGES: 1143-1152
        (G) DATE: 1992
        (H) DOCUMENT NUMBER:
        (I) FILING DATE:
        (J) PUBLICATION DATE: 1992
        (K) RELEVANT RESIDUES IN SEQ ID NO:

(xi) SEQUENCE DESCRIPTION: SEQ ID NO: 6:

TGGCAAGCCT ATGACATGGC CGGGGCCTGC CTCTCTCTGC CTCTGACCCT    50

(2) INFORMATION FOR SEQ ID NO: 7: -p53 DNA binding sequence:

(i) SEQUENCE CHARACTERISTICS:
        (A) LENGTH: 30
        (B) TYPE: nucleotides
        (C) STRANDEDNESS: unknown
        (D) TOPOLOGY: unknown (ii) MOLECULE TYPE: nucleic acids (iii) HYPOTHETICAL:

(iv) ANTI-SENSE:

(v) FRAGMENT TYPE:

(vi) ORIGINAL SOURCE:
        (A) ORGANISM: human
        (B) STRAIN:

```
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:   synthesized
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:  Foord, O., et al.
            (B) TITLE:
            (C) JOURNAL:  Mol. Cell. Biol.
            (D) VOLUME:  13
            (E) ISSUE:
            (F) PAGES:  1378-1384
            (G) DATE:  1993
            (H) DOCUMENT NUMBER:
            (I) FILING DATE:
            (J) PUBLICATION DATE:  1993
            (K) RELEVANT RESIDUES IN SEQ ID NO:

(xi) SEQUENCE DESCRIPTION: SEQ ID NO: 7:

GACACTGGTC ACACTTGGCT GCTTAGGAAT                                        30

(2) INFORMATION FOR SEQ ID NO: 8: p53 mutated DNA binding sequence:

(i) SEQUENCE CHARACTERISTICS:
            (A) LENGTH:  10
            (B) TYPE:  nucleotides
            (C) STRANDEDNESS:  unknown
            (D) TOPOLOGY:  unknown (ii) MOLECULE TYPE:  nucleic acids (iii) HYPOTHETICAL:

(iv) ANTI-SENSE:

(v) FRAGMENT TYPE:

(vi) ORIGINAL SOURCE:
            (A) ORGANISM:  human
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:   synthesized
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
```

(B) LOCATION:
        (C) IDENTIFICATION METHOD:
        (D) OTHER INFORMATION:

(x) PUBLICATION INFORMATION:
        (A) AUTHORS:  El-Deiry, W.S. et al.
        (B) TITLE:
        (C) JOURNAL:  Nature
        (D) VOLUME: 358
        (E) ISSUE:
        (F) PAGES:  83-86
        (G) DATE:  1992
        (H) DOCUMENT NUMBER:
        (I) FILING DATE:
        (J) PUBLICATION DATE:  1992
        (K) RELEVANT RESIDUES IN SEQ ID NO:

(xi) SEQUENCE DESCRIPTION: SEQ ID NO: 8:

AGGaATtCCT                                                                     10

P53AS PROTEIN AND ANTIBODY THEREFOR

STATEMENT REGARDING FEDERALLY SPONSORED RESEARCH

This invention was made with funding from the National Institute of Health Grant Number NIH RO1 CA 31101. The United States Government may have certain rights in this invention

BACKGROUND OF THE INVENTION

This is a Continuation-in-part of U.S. patent application Ser. No. 08/195,952, filed Feb. 11, 1994, now abandoned which is a Continuation-in-part of U.S. patent application Ser. No. 08/100,496, filed Aug. 2, 1993 now abandoned.

We have demonstrated previously that a wild type alternatively spliced p53 (p53as, for alternative splice) RNA exists in cultured cells and normal tissues at approximately 30% of the major p53 RNA form (Han and Kulesz-Martin, Nucleic Acid Res., 20:1979–81, 1992). The predicted protein encoded by the p53as transcript differs from p53 protein in 17 C-terminal amino acids and is truncated by 9 amino acids due to alternative splicing of intron 10 of the wild type p53 gene. Using antibody to the 17 C-terminal amino acids to detect p53as protein, we have demonstrated the following points. p53as protein is an alternatively spliced product of the wild type p53 gene. First detected in mouse epidermal cells, it is present in non-transformed and malignant cells. Like its major counterpart, p53 protein, it is located in the nucleus. However, while p53 antigen activity is primarily found in cells at the G1 stage of the cell cycle and is thought to play a role in G1 arrest in cells following treatment with DNA damaging agents, p53as is found in cells preferentially distributed in the G2 phase of the cell cycle and in a "tail" of cells with >G2 DNA content. These properties of p53as protein were suggestive of cellular functions distinct from the major p53 protein. The well established ability of the p53 protein to oligomerize and our finding of co-expression of p53as antigen activity with p53 in cells suggested potential for cooperation with p53 in its functions related to cell cycle control. This information is described in detail in the original patent application Ser. No. 08/100,496, filed Aug. 2, 1993 which is incorporated herein by reference.

The presence of the p53as protein in tumor cells and antibodies for its detection has applications in basic research on cell growth and differentiation. Presence of a homologous protein in human cells has applications in the diagnosis, prognosis and design of treatment strategy in human diseases of growth and differentiation such as cancer. The association with G2 suggests a functional role in G2 arrest and potential for gene therapy using the p53as coding sequence.

BRIEF DESCRIPTION OF THE INVENTION

The invention comprises plasmids and viral vectors containing an animal p53as cDNA sequence. The p53as for which a cDNA sequence is provided may be a naturally occurring or synthetic p53as. A form of natural p53as is present in normal cells of at least some mammals. p53as is essentially identical to known normal growth controlling protein p53, at least until the final 50 and preferably until the final 30 amino acids of the carboxy terminal end of the protein. "Essentially identical" means at least 80% and preferably at least 90% sequential correspondence with p53. It should be noted that mouse p53 has an 81% identity with mouse p53as at the protein level. Mouse p53as has a highly acidic N terminus, a basic C-terminus and a central region containing uncharged amino acids.

The final 50 amino acids of p53as protein proximate the carboxy terminus of the p53as protein, are at least partly different than the final 50 amino acids of p53 protein. The difference is believed to be at least in part due to different amino acid sequences in the two proteins proximate the carboxy termination of the protein and may also be partly due to a longer or shorter p53as amino acid chain when compared with p53. It is believed that the most common and probable final few amino acids at the carboxy termination of naturally occurring p53as contain the sequences SPNC and SPPC.

p53as has been found to function as a growth regulator in all mammals tested regardless of whether or not p53as has been found to naturally occur in the mammal.

It is to be understood that p53as may be of natural or synthetic form, provided that, at a minimum, terminal amino acids differ from the 50 terminal amino acids of p53 so that the modified products will act the same as active p53 protein and is functionally equivalent to mouse p53as protein.

In general, it can be stated that p53as is functionally the same as p53 except that a p53as lacks the negative regulatory domain for p53 sequence specific DNA binding which is found within the last 50 amino acids at the p53 C terminus. The negative regulatory domain of p53 negates p53 sequence specific binding in certain cellular environments which in turn causes p53 to lose activity. p53as lacks the negative regulatory domain and thus remains active in similar cellular environments. To obtain a p53as the terminal amino acids of p53 are preferably modified, i.e., there is at least some substitution, as opposed to simple truncation. A portion of a preferred p53as sequence may be identified to a position of wild type p53 gene from the same animal. In preferred embodiments, the p53as is a mouse p53as.

A preferred viral vector is baculovirus vector. The invention further includes antibodies both polyclonal and monoclonal, to p53as and to at least a portion of human p53 intron 10 sequence encoding SLRPFKALVREKGHRPSSHSC SEQ. ID. NO. 1 which is related to p53as sequences and plasmids and viral vectors containing such sequences.

All of the above find utility in studying p53 and p53as and their relative expressions which is believed important for detection and control of malignant cells and their susceptibility to treatment agents.

The antibodies can detect the presence of p53as and related sequences and when injected into cells could cause cell cycle arrest and the plasmids and viral vectors, with appropriate promoters, can cause expression of the p53as and p53 intron 10 sequences which can affect cell growth and perhaps arrest certain malignancies.

BRIEF DESCRIPTION OF THE DRAWINGS

FIG. 2. p53as protein binds specifically and efficiently to DNA. Binding of p53as protein translated in vitro (5 µl of 250 µl reaction) to $^{32}$P-labeled oligonucleotide (ng) in the presence of increasing amount of unlabeled wt p53 binding sequence (wt) or of mutated (mut) sequence (see [1] in Materials and Methods) demonstrates the specificity of p53as protein for the p53 binding motif. 200 ng ApAs antibody to p53as can super-shift the binding complex. 200 ng of pre-immune rabbit serum (Pre) and PAb421 (421) were used as controls.

FIG. 3. p53as protein complex with DNA is shifted by anti-p53as (ApAs) and abrogated by anti-p53 antibodies PAb246 (246) and CM5 but not mutant conformation-specific PAb240 (240). p53as protein was translated in vitro in reticulocyte lysates and assayed by EMSA for binding to $^{32}$P-labeled probe in the absence of antibodies (−) or in the presence of PAb421, 200 ng PAb246 and rabbit polyclonal anti-p53 antibody CM5, or 200 ng ApAs. IgG2a (IgG), pre-immune serum (Pre), and non-programmed reticulocyte lysate (Lys) were used as controls.

FIG. 4. p53 protein requires activation to bind to DNA. There is no apparent binding to the $^{32}$P-labeled probe by p53 (lanes 2–6, 8–10) as compared to the non-programmed rabbit reticulocyte lysate (lane 1). A binding complex can be detected when 200 ng of PAb421 was included in the reaction (lane 7).

FIG. 5. Interaction of p53as with p53 and its effects on DNA binding activity of p53as. Equal amount of in vitro transcribed p53 and p53as RNAs were co-translated (AP) or translated individually and p53 (P) and p53as (AS) proteins were assayed for their DNA binding activities by EMSA. The co-translated proteins have lower DNA binding activities (lane 1) than p53as alone (lane 8). Two binding complexes can be detected when 200 ng PAb 421 (lane 2) or 200 ng PAb 421 plus ApAs (lane 4) were included in the reactions containing co-translated proteins, while only one binding complex appears as PAb 421 activates p53 DNA binding activity (lane 7). 200 ng ApAs did not cause any apparent supershift for co-translated proteins (lane 3). Two higher molecular weight binding complexes can be seen when ApAs was added to the reaction containing only p53as protein (lane 9).

FIG. 6. Lack of interaction of p53as and p53 proteins mixed posttranslationally. Equal amounts of p53 and p53as translated in vitro were mixed and assayed for binding to $^{32}$P-labeled oligonucleotide by non-denaturing polyacrylamide gel electrophoresis (lane 1). 200 ng each of the indicated antibodies were added to the binding reaction.

FIG. 8. Insect cells arrest in the G2 phase of the cell cycle after infection with a baculovirus vector containing the full length p53as cDNA.

FIG. 9. Mouse squamous cell carcinoma cells arrest in the G2 phase of the cell cycle after transfection with a plasmid construct containing p53as cDNA

DETAILED DESCRIPTION OF THE INVENTION

Figure 1:
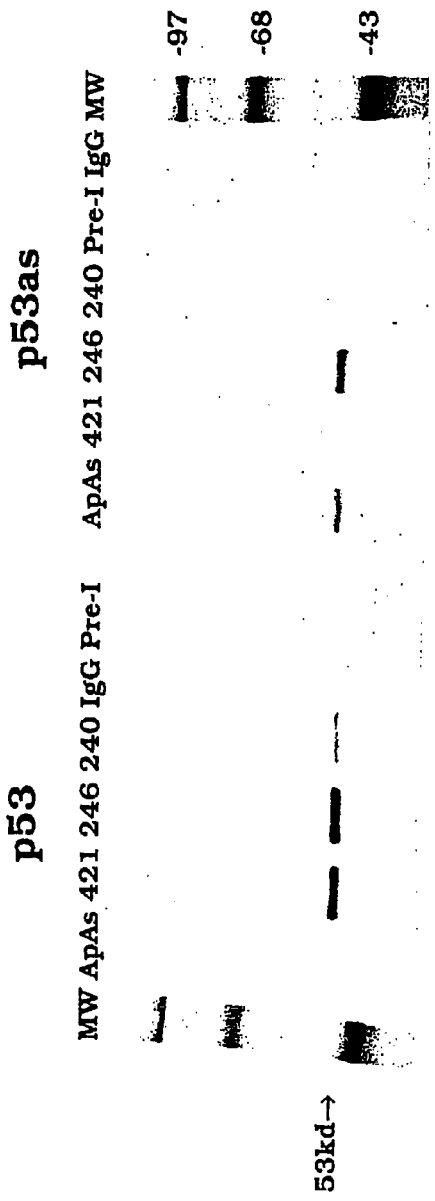
FIG. 1. shows immunoprecipitation of proteins translated in vitro: PAb421 is specific for the major p53 form only, and ApAs is specific for p53as protein only. 10 µg of plasmid pBSp53as or pBSp53 was linearized by BamHI and transcribed with 20 Units T3 RNA polymerase. The in vitro translation was performed according to a standard protocol (Promega) by incubating 3 µg RNA with 35 µl of rabbit reticulocyte lysate in the presence of 4 µl (40 µCi) $^{35}$S-methionine for labeling of proteins. For co-translation of p53as and p53, an equal amount of each RNA was incubated with rabbit reticulocyte lysate (Promega). Immunoprecipitation was performed by incubating 5 µl $^{35}$S-labeled protein with 1 µg PAb421, ApAs or PAb246 at 4° C. overnight. Protein A-Sepharose 4B was then added with gentle mixing at 4° C. for 2 hr. After centrifugation, the pellets were washed three times with Net-gel buffer. The pellets were suspended in 2× sample buffer containing 100 mM DTT and separated by electrophoresis in a 7.5/o SDS-polyacrylamide minigel. The gel was enhanced, dried and exposed overnight to Kodak X film. Two lysate reactions are shown, p53 or p53as RNA—see labels at top. Antibodies used to immunoprecipitate protein from each lysate reaction are indicated.

Materials and Methods for the DNA binding studies.
Plasmids for in vitro transcription and translation of p53as and p53 proteins.

Plasmids containing the cDNA sequence unique to p53as are included in this invention. One such plasmid is pBSp53as which contains full length alternatively spliced p53 cDNA. pBSp53as was constructed from p53 cDNA beginning at nt-11 of the (where 1 is the first ATG encoding methionine) and ending at nt 1539, cloned into the EcoRI and BamHI sites of pBluescript SK under the control of a T3 phage promoter. The N-terminal fragment of wt p53 was amplified by reverse transcriptase/polymerase chain reaction (RT-PCR) from a mouse epidermal cell RNA template and the C-terminal fragment of p53as was amplified by PCR from plasmid p6.4 (which contains an alternatively spliced p53 cDNA; Han and Kulesz-Martin, Nucl. Acids Res. 20: 1979–81, 1992) using primers which contained a StuI restriction site at the 5'end of the sense primer (AGTCAGGCCTTAGAGTTAAAGGATGC-CCATGCTACAGA) SEQ. ID. NO. 2 and a BamHI site at the 5' end of the antisense primer. pBSp53 was made from pBSp53as by replacement of the StuI/BamHI C-terminal fragment of p53as cDNA with the StuI/BamHI segment of wild type p53 cDNA from plasmid pLSVNc51 (ref. Oren). In particular, cDNA for the N-terminus of p53 (nt-111 to 1090) was made using template RNA from 291 nontransformed epidermal cells by means of a reverse transcriptase reaction, amplified by PCR and cloned into the EcoRI and BamHI sites of pBluescript SK under the control of a T3 phage promoter to create plasmid pBSRS13. The primers used for PCR were: sense, AGTC-GAATTCATTGGGACCATCCTGGCT, SEQ. ID. NO. 3 antisense, AGTCGGATCCTGGAGTGAGCCCTGCT-GTCT SEQ. ID. NO. 4. These primers contained an EcoRI restriction site at the 5' end of the sense primer and a BamHI site at the 5' end of the antisense primer (denoted by underlining). The C-terminal p53 cDNA (nt1028 to 1539) was amplified by PCR from plasmid p6.4 (which contains an alternatively spliced p53 cDNA) using primers which contained a StuI restriction site at the 5' end of the sense primer (AGTCAGGCCTTAGAGTTAAAGGATGC-CCATGCTACAGA) SEQ. ID. NO. 2 and a BamHI site at the 5' end of the antisense primer (as in Han and Kulesz-Martin, Nucl. Acids Res. 20: 1979–81, 1992). The StuI to BamHI segment of this PCR reaction product was then ligated to the StuI and BamHI sites of plasmid pBSRS13 to create plasmid pBSp53as, containing a full length alternatively spliced p53 cDNA. To construct pBSp53, the StuI and BamHI fragment from wt p53 cDNA was substituted for the StuI and BamHI fragment of the p53as cDNA in pBSp53as.

In vitro transcription and translation.

10 μg of plasmid pBSp53as or pBSp53 was linearized by BamHI and transcribed with 20 Units T3 RNA polymerase for immunoprecipitation studies and DNA binding studies. The in vitro translation was performed according to a standard protocol (Promega) by incubating 3 μg RNA with 35 ul of rabbit reticulocyte lysate. For immunoprecipitations, 4 ul (40 μCi) $^{35}$S-methionine was used for labeling of proteins. For co-translation of p53as and p53, an equal amount of each RNA was incubated with rabbit reticulocyte lysate (Promega).

Immunoprecipitation was performed by incubating 5 μl $^{35}$S-labeled protein with 1 μg PAb421, ApAs or PAb246 at 4° C. overnight. Protein A-Sepharose 4B was then added with gentle mixing at 4° C. for 2 hr. After centrifugation, the pellets were washed three times with Net-gel buffer. The pellets were suspended in 2× sample buffer containing 100 mM DTT and separated by electrophoresis in a 7.5% SDS-polyacrylamide minigel. The gel was enhanced, dried and exposed overnight to Kodak X film. Two lysate reactions are shown, p53 or p53as RNA—see labels at top. Antibodies used to immunoprecipitate protein from each lysate reaction are indicated.

For the DNA binding assay, 3 ug of sense RNA for p53 or p53as was added to 35 ul reticulocyte lysate and adjusted to a total volume of 50 ul for translation in vitro. For cotranslations, half the amount of each RNA was used. An aliquot of 5 ul of translation mixture (or 2.5 ul each lysate for the mixing experiments) was incubated with 2 ug poly [d(I-C)] and 30,000 cpm (approximately 1 ng) of $^{32}$P-end-labeled DNA probe in 20 ul DNA binding buffer (0.1/o Triton x-100, 4% glycerol, 1 mM EDTA, 5mMDTT, 20 mM Tris-HCl, pH 7.2, 80 mM NaCl) at 4 C for 20 min. Where indicated, 200 ng of antibody was included in the reaction. Reaction products were separated on a 4% neutral polyacrylamide gel in 0.5×TBE buffer. The gel was dried and labeled binding complexes were visualized by radioautography.

Results, p53as Protein Binding to DNA

As presented in the original patent application, we suggested that p53as protein would be active for binding to DNA. DNA binding of the major p53 form is considered essential for its function as a cell cycle control gene. DNA binding is required for its activity as a transcription factor which controls the expression of other genes. The interaction of p53 with other proteins is of intense interest in the scientific community because such p53-associated factors may control the activity of p53 by affecting its binding to DNA. The data presented herein demonstrates that p53as protein binds to DNA, and that p53as and p53 protein associate with each other, suggesting that p53as is a newly discovered p53-associated protein.

The p53as protein has lost basic amino acids but has retained acidic amino acids important for oligomerization. The sequence-specific DNA binding activity of p53as protein translated in vitro, separately, or cotranslated with p53 protein, was studied in an attempt to answer the following questions: 1) does p53as protein, like the major p53 form, have sequence-specific DNA binding activity? and 2) does p53as protein interact with p53, modulating its ability to form a complex with DNA?

Figure 2:
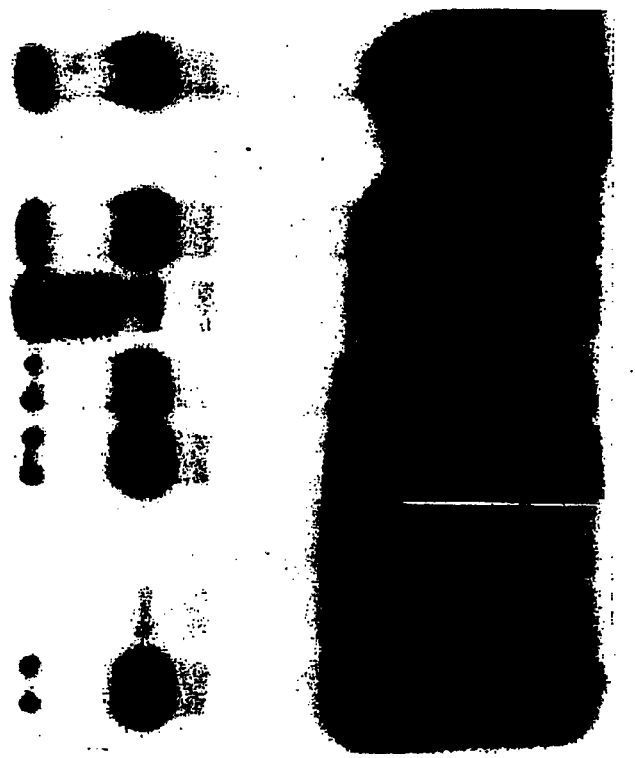
FIG. 2 through FIG. 6 represent electrophoretic mobility shift assays (EMSA) of p53 and p53as proteins translated in vitro using the DNA probe sequence presented in Table 2.

To answer these questions, specific antibodies to p53 and to p53as proteins were used (Table 1). The specificity of the antibodies was tested by competition with the p53as peptide as reported in the original patent application. Further evidence for specificity of the p53as antibody is reactivity of anti-p53as with p53as protein translated in vitro but not with the major p53 protein. The commercially available antibody PAb421 which is specific for an epitope lacking in p53as reacted with p53 protein translated in vitro but not with p53as protein (FIG. 2.) This ensured that these antibodies would not cross react with the two proteins in the DNA binding assays. Therefore, the ability of the anti-p53as antibody to shift a complex between in vitro translated p53as protein or p53+p53as cotranslated protein clearly indicates that p53as protein must be present in the protein/DNA complex.

Figure 3:

In order to answer the first question above, electrophoretic mobility shift assays were performed using a $^{32}$P-labeled double-stranded oligonucleotide probe corresponding to the p53 binding sequence shown in Table 2. As shown in FIG. 2, p53as protein translated in vitro gave a strong signal representing a shift from free probe (dark signal at bottom of figure) to a higher molecular weight complex composed of protein and the labeled DNA probe. The p53as protein bound specifically to the p53 binding sequence, as shown by loss of the band with unlabeled competing DNA probe (wt) being included in the reaction but not with unlabeled oligonucleotide corresponding to the mutated p53 binding sequence (mut). (Note that the first weak band above the free probe is nonspecific). The identity of the shifted band as a complex containing p53as is shown by supershifting of the p53as/DNA complex by anti-p53as antibody (ApAs) but not by preimmune serum (Pre) or anti-p53 antibody PAb421. The supershift of p53as protein by ApAs resulted in two higher molecular weight bands. Further verification of the ApAs reactive protein as a product of the p53 gene is provided in FIG. 3 by loss of the signal in the presence of anti-p53 antibodies PAb246 and CM5, which react with both p53 and p53as proteins.

Figure 4:
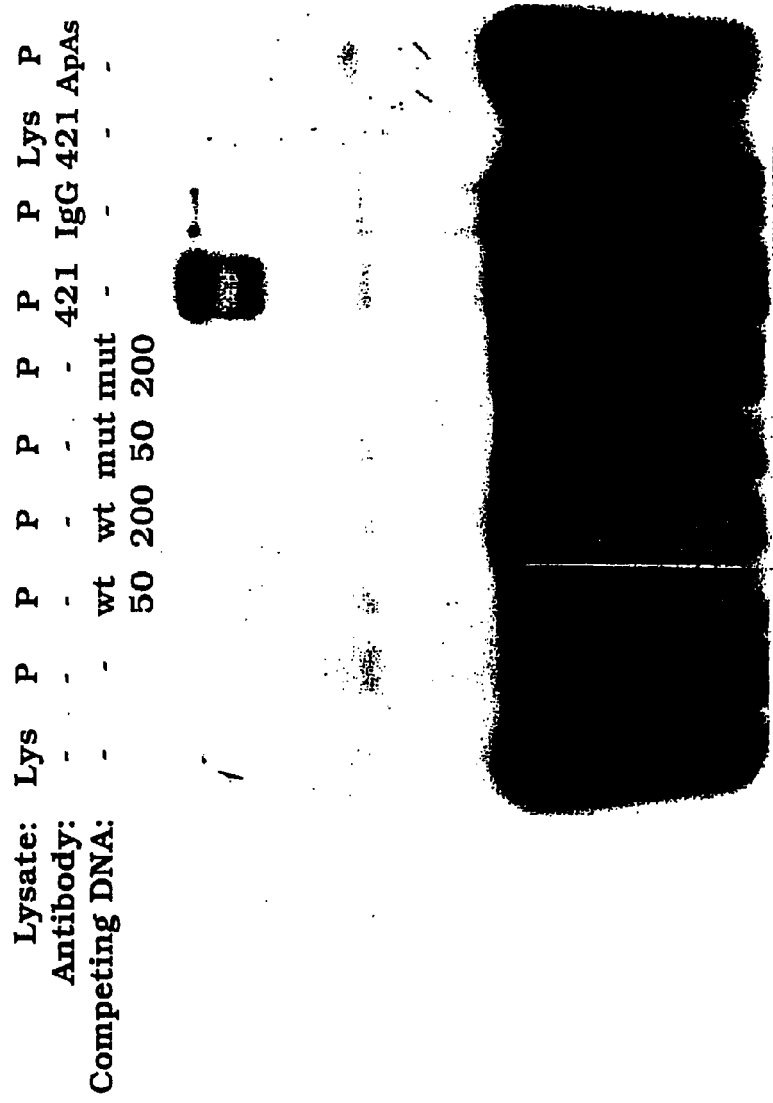

In contrast, the binding of the major p53 form to specific DNA binding sequences is inefficient and requires activation (Hupp, et al., 1992). FIG. 4 demonstrates that the major p53 form translated in vitro is not active for DNA binding but required activation by PAb421. Activated p53 bound to DNA and resulted in a supershift of a single high molecular weight complex.

Figure 5:
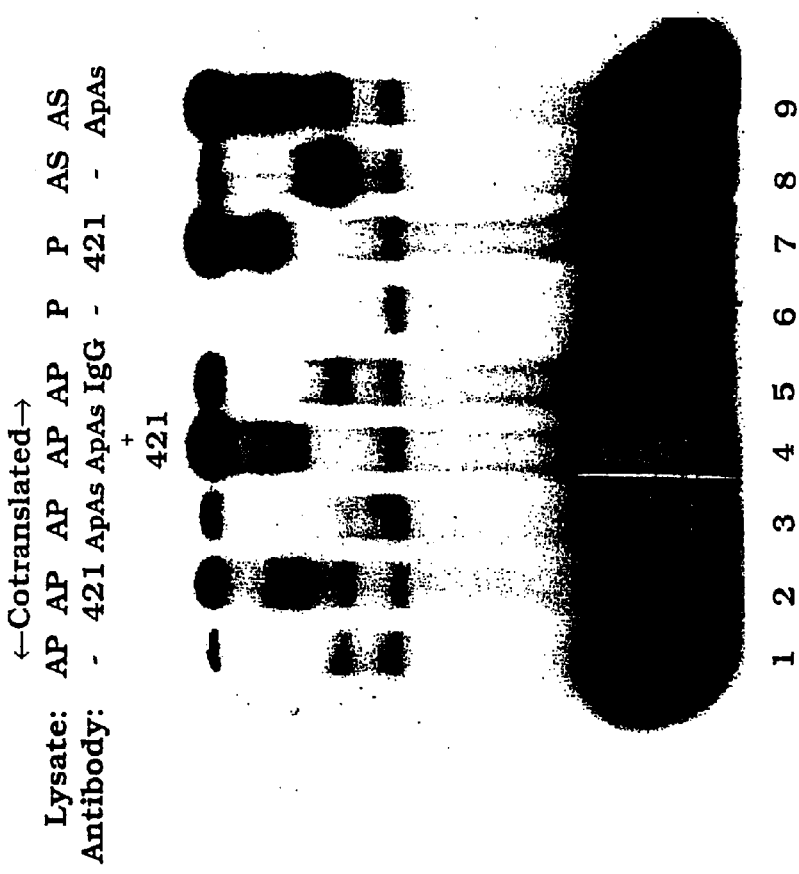

Because p53 has been reported to self-associate to form oligomers, for example dimers and tetramers (Stenger et al., 1992), and because p53as has retained acidic amino acids but not basic amino acids important for dimer and tetramer formation, the DNA binding of p53 and p53as proteins, translated together or mixed after separate translation, was examined. As shown in FIG. 5, cotranslated p53 reduced the signal for DNA binding compared to p53as alone. This appears to be due to a direct association of p53 and p53as proteins because PAb421 antibody now resulted in a a supershift of two bands rather than the one obtained with p53 alone.

Figure 6:
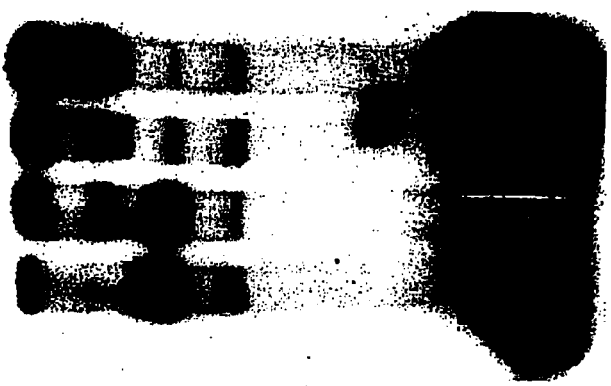

In contrast to cotranslation of p53 and p53as proteins, mixture of lysates containing each protein translated individually did not show inactivation of p53as by p53 protein for DNA binding, and PAb421 supershifted only one band, suggesting that p53 and p53as must be translated together for association to occur (FIG. 6). This is consistent with the report that oligomerization between human p53 and mouse p53 occurs when they are cotranslated, but not when mixed (Milner and Medcalf, 1991).

Figure 7:
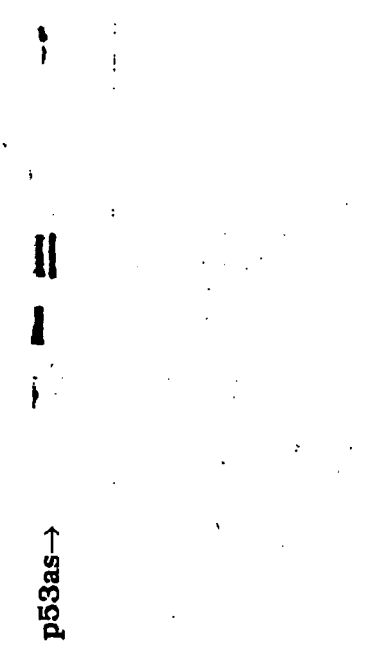
FIG. 7. Heteroligomers of p53 with p53as identified by immunoprecipitation followed by immunoblotting. In vitro translated proteins were p53as (AS), p53 (P), cotranslated p53 and p53as (AP) or a mixture of p53as plus p53 translated individually (A+P) and non-programmed reticulocyte lysate control (Lys). The translated proteins (15 µl each lysate, 30 µl for cotranslation) were immunoprecipitated with anti-p53 antibody PAb421 (421) rabbit antibody to p53as (ApAs), pre-immune (Pre) or IgG2a (IgG) controls. The immune complexes were fractionated on a 10% SDS-polyacrylamide minigel, transferred to a nitrocellulose membrane and incubated with horseradish peroxidase-conjugated ApAs for 1 hour. The p53as was visualized through chemiluminescence (ECL, Amersham, Arlington Heights, Ill.).

In order to directly test the ability of p53 protein to form a complex with p53as protein, immunoprecipitation of cotranslated proteins was done using. PAb421 and the immunoprecipitated proteins were resolved by denaturing gel electrophoresis, blotted and exposed to ApAs antibody. Proteins in complex with the protein immunoprecipitated by the specific antibody will also precipitate. Proteins not in complex will not. The lower band in the immunoblot shown in FIG. 7 is the p53as band. These results indicated that cotranslated p53as and p53 proteins contain complexes of p53 and p53as immunoprecipitable by PAb421 and blotted by ApAs. A much weaker signal is generated in mixtures of p53 and p53as proteins translated individually, indicating that for stable complexes to form the proteins must be cotranslated.

Summary and Interpretations of DNA Binding Studies p53as protein exhibited the antibody binding properties of wild type p53 protein, PAb246+, PAb240−, but lacked the C-terminal epitope reactive with PAb421. p53as protein translated in vitro was activated for binding to a p53 DNA binding sequence. The major p53 protein, in contrast, required activation for DNA binding (by monoclonal antibody PAb421). There appears to be a direct interaction between p53as and p53 proteins which influenced the composition of the DNA binding complex and the magnitude of DNA binding. Because cotranslated p53 protein inactivated p53as protein for DNA binding, and because two bands were super-shifted by PAb421 in lysates containing p53as and p53 cotranslated proteins, compared to one band in lysate containing p53 alone. These results could be explained by binding to DNA of p53as and p53/p53as heterooligomers, in addition to the binding of p53.

The significance of these findings is that they are consistent with a functional role for p53as protein in cells, which may, at least in part, be distinct from the function(s) of the major p53 protein form. Considering that vectors and plasmids containing the p53 gene are being tested for applications in gene therapy, and considering the results herein that p53as is active for binding to a p53 binding sequence and that p53as interacts with p53, resulting in altered DNA binding, plasmids and vectors for the expression of mouse and human p53as in cells and for uses in gene therapy in humans are claimed herein.

Cellular Function of p53as

In the original patent application the association of p53as antigen activity with cells distributed primarily in the G2 phase of the cell cycle was presented. This was an important clue that p53as might have a distinct function compared to p53 protein. In order to examine whether p53as protein might have a direct role in cell cycle arrest, a DNA sequence containing the entire coding sequence of p53as was constructed. This sequence in different from the p53 coding sequence, as presented in the original patent application, and is different from previously reported DNA constructs. Constructs containing the p53as cDNA were expressed in insect cells and in mammalian cells and effects on the cell cycle distribution of cells were evaluated.

Materials and Methods for p53as Expression Studies

Insect Cells

Methods were per manufacturers instructions (Invitrogen) and materials and included linear AcMNPV DNA and transfer vector (e.g. pVL 1392, pVL 1393) and insect cell line *S. frugiperda* Sf9, propagated at 27 C in Grace's supplemented insect medium containing 10% fetal bovine serum (GIBCO) and 10 ug/ml gentamycin sulfate. pVL1393BGB53 baculovirus vector containing wt p53 cDNA was constructed by inserting the BglII/BamHI fragment of pLSVNc51 (including the entire wt p53 cDNA) into the pVL 1393 vector. pVL1393Asp baculovirus vector (containing p53as cDNA) was constructed by replacement of the StuI/BamHI C-terminal fragment of p53as cDNA (Han and Kulesz-Martin, Nucl. Acids Res. 1992) with the BamHI/StuI fragment of the pVL1393BGB53 vector (see above). To purify recombinant viruses, Sf9 cells were cotransfected with linear AcMNPV DNA and the transfer vector containing p53as and grown for 3 days. Recombinant viruses were identified by plaque assays or serial dilutions. Alternatively, p53 and p53as baculovirus contructions will be cotransfected with linearized (PharMingen) virus DNA which allows propagation of only recombinant virus. Virus stocks which resulted in p53as expression in insect cells (assayed by immunoblotting using anti-p53as antibody) were expanded and used to infect insect cells for the flow cytometry studies.

Baculovirus pVL1393Asp stock was added to insect cell cultures at $3\times10^6$ cells/60 mm dish. After several (2 to 4) days, cells were harvested by trypsinization and stained with anti-p53 as antibody and analyzed by flow cytometry as detailed in the original patent application.

Mammalian Cells

Plasmids

Plasmids for expression of p53as in mammalian cells were constructed. An example is given of the full length p53as cDNA under the control of a metallothionein promoter. However, other promoters which may increase or decrease expression in given cell types, such as the cytomegalovirus promoter, will be used as appropriate. pmMTBGB containing the full length wild type p53 cDNA beginning at −67 nt (where nucleotide 1 is the first nucleotide of the first ATG codon) was constructed by replacement of the BglII/BamHI fragments of plasmid pmMTval53cG (from M. Oren) with the BglII/BamHI fragment of plasmid pLSVNc51 noted above. The pmMTAsp plasmid was constructed by firstly, replacement of the XhoI/BamHI fragment of pmMTBGB with the XhoI/BamHI fragment of pVL1393Asp and secondly, introduction of a BamHI fragment from plasmid BCMGNeo (Karasuyama and Melchers, 1988) containing the splicing signals and polyA tail of the rabbit B-globin gene.

Transfection

Mouse squamous cell carcinoma cells (291.05RAT) were plated in culture medium at 2 to $3\times10^6$ per 60 mm dish and transfected with plasmid pmMTAsp when 40 to 60% confluent using Lipofectin (GIBCO BRL). 10 ug of plasmid diluted in 100 ul ddH$_2$O was mixed with 30 ul Lipofectin adjusted to 1 ml with serum-free culture medium, incubated with the cell cultures for 20 hr, then removed and replaced with culture medium with serum. 24 hr later CdCl$_2$ was added to the cells to stimulate transcription of p53as mRNA from the plasmid DNA and enhance the expression of p53as protein. Two days later, cells were harvested by trypsinization, stained with anti-p53as antibody and analyzed by flow cytometry as described in the original patent application.

Results of p53as Expression Studies

Insect Cells

Approximately 12% of insect cells infected with the baculovirus vector containing p53as expressed p53as antigen activity compared to 0% of insect cell controls lacking exogenous p53as cDNA. Insect cells expressing p53as protein were primarily in the G2 phase of the cell cycle or in a "tail" representing cells containing >G2 DNA content (FIG. 8). Control insect cells were primarily distributed in the G1 phase of the cell cycle.

The significance of these studies is likely to be relevant to cell cycle control in mammalian cells. Other cells which do not have the p53 gene have proven very useful for studies of the role of p53 protein in cell cycle control. For example, while yeast does not contain the p53 gene, studies of p53 in yeast have been done to take advantage of the knowledge of cell cycle checkpoints and cell cycle regulatory proteins gained using the yeast model. The studies in yeast have been very informative, since p53 protein behaves in yeast cells in a manner consistent with its cell cycle role in mammalian cells (Nigro et al., 1992; Bischoff et al., 1992).

Mammalian Cells

As in the case of the insect cells, mouse carcinoma cells transfected with the plasmid containing p53as cDNA were preferentially distributed in the G2 phase of the cell cycle or in a "tail" representing cells containing >G2 DNA content (FIG. 9).

Summary and Interpretations of p53as Expression Studies

These data indicate that expression of p53as by introduction into cells leads to accumulation of cells in the G2 phase of the cell cycle or exit from the cycle to a state in which DNA content is greater than G2 cells. A likely explanation for this is an arrest of cells within G2 and failure to undergo mitosis and proceed to the G1 or G0 phase of the cycle.

Significance of p53as Expression Studies

These data are consistent with a checkpoint function of p53as at the G2/M phase of the cell cycle. Activity of p53as expression in causing cells to exit from the cell cycle would have useful applications in gene therapy of proliferative disorders such as cancer or psoriasis.

Because human and mouse p53 proteins form complexes in cells, the construct containing mouse p53as cDNA is claimed for the purposes of gene expression in mammalian cells and nonmammalian cells for research purposes, including human cells, and for gene therapy in humans. In addition, a purified plasmid construct containing the human p53as homologue of mouse p53as, defined by insertion of human intron 10 sequences into a sequence containing wt p53 DNA (as defined in original patent application Ser. No. 08/100,486) is claimed for research purposes in mammalian and nonmammalian cells, and for gene therapy in humans.

Table 1. shows reactivities of antibodies against p53 proteins. Mouse p53 has 390 amino acids; human p53 393 amino acids. All antibodies are mouse monoclonals commercially available from Oncogene Science, Cambridge Mass., except ApAs rabbit polyclonal specific for p53as protein which was made in Dr. Kulesz-Martin's laboratory, RPCI. Sources: Oncogene Science Catalogue, p. 8, 1992; Vajtesek et al., J. of Immunolog. Methods 151:237–244, 1992, [a]Wade-Evans, A. and Jenkins, J. R. EMBO J., 4:699–706, 1985, [b]Gannon, EMBO, 9:1595–1602, 1990, [c]Stephen, C. W. and Lane, D. P., J. Mol. Biol., 5:577–583, 1992 and [d]Kulesz-Martin et al., Mol. Cell. Biol., in press, March 1994.

Table 2. shows p53 DNA Binding Sequences used for assay of p53as protein binding activity.

TABLE 1

Reactivities of Antibodies Against p53 Proteins

| Ab | Species | wt conform | wt denatured | mutated | p53 | p53as | epitope | IP | WIB | cell staining | frozen sections | paraffin sections |
|---|---|---|---|---|---|---|---|---|---|---|---|---|
| PAb421[a] | mu/hu | + | + | + | + | − | 370–378 | + | +/− | + | + | − |
| Pab246[a] | mu | + | − | − | + | + | 88–109 | + | − | + | + | nt |
| PAb240[bc] | mu/hu | − | + | + | + | (−) | 210–214 | + | + | + | + | − |
| ApAs[d] | mu | + | + | nt | − | + | (364–381) | + | + | + | nt | nt |

Mouse p53 has 390 amino acids; human p53 393 amino acids. All antibodies are mouse monoclonals commercially available from Oncogene Science, Cambridge Mass., except ApAs rabbit polyclonal specific for p53as protein which was made in Dr. Kulesz-Martin's laboratory, RPCI. Sources: Oncogene Science Catalogue, p. 8, 1992; Vajtesek et al., J. of Immunolog. Methods 151:237–244, 1992, [a]Wade-Evans, A. and Jenkins, J. R. EMBO J., 4:699–706, 1985, [b]Gannon, EMBO, 9:1595–1602, 1990, [c]Stephen, C. W. and Lane, D. P., J. Mol. Biol., 5:577–583, 1992 and [d]Kulesz-Martin et al., Mol. Cell. Biol., in press, March 1994.

TABLE 2

Known p53 DNA Binding Sequences.

```
1. (Pu)3-C(A/T)(A/T)G-(Py)3/(Pu)3-C(A/T)(A/T)G-(Py)3
p53 binding sequence
AGGCATGCCT/AGGCATGCCT                                        SEQ ID NO:5
mutated sequence used for negative control (small
letters indicate nucleotide substitutions)
AGGaATtCCT/AGGaATtCCT                                        SEQ ID NO:8
Ref.: El-Deiry, W. S., Kern, S. E., Pietenpol, J. A.,
Kinzler, K. W. and Vogelstein, B. (1992) Nature 358,
83-86.

2. TGGCAAGCCTATGACATGGCCGGGGCCTGCCTCTCTCTGCCTCTGACCCT        SEQ. ID. NO.6
Ref.: Zambetti, G., Bargonetti, J., Walker, K.,
Prives, C., and Levine, A. (1992) Gene & Development
6, 1143-1152

3. GACACTGGTCACACTTGGCTGCTTAGGAAT                            SEQ. ID. NO.7
Ref.: Foord, O., Navot, N., and Rotter, V. (1993)
Mol. Cell. Biol. 13(3), 1378-1384
```

---

What is claimed is:

1. A plasmid containing a cDNA sequence which encodes a protein designated p53as, said p53as being sequentially the same as wildtype p53 up to the final 50 carboxy terminal amino acids of p53, said p53as being different than p53 within the final 50 carboxy terminal amino acids of p53 so as to lack a negative regulatory domain of p53 for p53 sequence specific DNA binding found within the last 50 amino acids at the p53 carboxy terminus, which negative regulatory domain must be activated in p53 for p53 to have active DNA binding, said p53as and activated p53 binding to the same p53 DNA binding sequence AGGCATGCCT/AGGCATGCCT SEQ ID NO: 5 and said p53as being different than p53 within the final 50 carboxy terminal amino acids of p53 so as to provide an epitope within said p53as which gives rise to an antibody which is reactive with the p53as but not with p53.

2. The plasmid of claim 1 wherein the p53as naturally occurs in a mammal.

3. The plasmid of claim 1 wherein the p53as is mouse p53as.

4. A viral vector containing a cDNA sequence which encodes a protein designated p53as, said p53as being sequentially the same as wildtype p53 up to the final 50 carboxy terminal amino acids of p53, said p53as being different than p53 within the final 50 carboxy terminal amino acids of p53 so as to lack a negative regulatory domain of p53 for p53 sequence specific DNA binding found within the last 50 amino acids at the p53 carboxy terminus, which negative regulatory domain must be activated in p53 for p53 to have active DNA binding, said p53as and activated p53 binding to the same p53 DNA binding sequence AGGCAT-GCCT/AGGCATGCCT, SEQ ID NO.5, and said p53as being different than p53 within the final 50 carboxy terminal amino acids of p53 so as to provide an epitope within said p53as which gives rise to an antibody which is reactive with the p53as but not with p53.

5. The viral vector of claim 4 wherein the vector is baculovirus vector.

6. The viral vector of claim 4 wherein the p53as naturally occurs in a mammal.

7. The viral vector of claim 5 wherein the p53as naturally occurs in a mammal.

8. The viral vector of claim 4 wherein the p53as is mouse p53as.

9. The viral vector of claim 5 wherein the p53as is mouse p53as.

10. A plasmid containing a p53as gene sequence encoding the peptide SLRPFKALVREKGHRPSHSC SEQ ID NO: 1.

11. The plasmid of claim 1 containing a p53as gene sequence encoding a portion of the peptide SLR-PFKALVREKGHRPSHSC, SEQ ID NO: 1, which peptide will raise an antibody response which gives rise to an antibody which is reactive with the p53as but not with p53.

12. A cell transfected with the plasmid of claim 1.

13. A cell transfected with the viral vector of claim 4.

14. The viral vector of claim 4 containing a p53as gene sequence encoding a portion of the peptide SLR-PFKALVREKGHRPSHSC, SEQ. ID.D NO. 1, which peptide will raise an antibody response which gives rise to an antibody which is reactive with the p53as but not with p53.

* * * * *